(12) United States Patent
Fraser et al.

(10) Patent No.: US 6,716,812 B1
(45) Date of Patent: Apr. 6, 2004

(54) MODULATION OF SPERM FUNCTION

(75) Inventors: Lynn Repsis Fraser, Rickmansworth (GB); Marc Dean Pondel, Sutton (GB)

(73) Assignee: King's College London (GB)

( * ) Notice: Subject to any disclaimer, the term of this patent is extended or adjusted under 35 U.S.C. 154(b) by 0 days.

(21) Appl. No.: 09/857,131

(22) PCT Filed: Dec. 1, 1999

(86) PCT No.: PCT/GB99/04022

§ 371 (c)(1),
(2), (4) Date: Aug. 3, 2001

(87) PCT Pub. No.: WO00/32224

PCT Pub. Date: Jun. 8, 2000

(30) Foreign Application Priority Data

Dec. 2, 1998 (GB) .............................................. 9826541

(51) Int. Cl.[7] .............................................. A61K 38/00
(52) U.S. Cl. .......................... 514/2; 530/307; 530/852; 435/2; 435/806
(58) Field of Search ................................ 530/307, 852; 435/2, 806; 600/35

(56) References Cited

PUBLICATIONS

Gnessi "Salmon Calcitonin Inhibits Human Sperm Motility in Vitro" 1984, Biochemical and Biophysical Research Communications, vol. 125, No; 1, pp. 199–204.*
Fraser LR. (1993) In vitro capacitation and fertilization. *Methods Enzymol* 225, 239–253.
Gnessi L, Silvestroni L, Baffri A, Moretti C, Panerai AE, Bonifacio V & Fraioli F. (1984) Salmon calcitonin Inhibits human sperm motility in vitro. *Biochem Biophys Res Commun* 125, 199–204.
Green CM, Cockle SM, Watson PF & Fraser LR. (1994) Stimulating effect of pyroglutamylglutamylprolineamide, a prostatic, TRH–related tripeptide, on mouse sperm capacitation and fertilizing ability in vitro. *Mol Reprod Dev* 38, 215–221.

Green CM, Cockle SM, Watson PF & Fraser LR. (1996) Fertilization promoting peptide, a tripeptide similar to thyrotrophin–releasing hormone, stimulates the capacitation and fertilizing ability of human sperm in vitro. *Human Reprod* 11, 830–836.

Hilton JM, Mitchelhill K, Pozvek G, Dowton M, Quiza M, Sexton P. (1998) Purification of calcitonin–like peptides from a rat brain and pituitary. *Endocrinology* 139, 982–992.

Pozvek G, Hilton JM, Quiza M, Houssami S & Sexton PM. (1997) Structure/function relationships of calcitonin analogues as agonists, antagonists, or inverse agonists in a constitutively activated receptor cell system. *Mol Pharmacol* 51, 658–665.

Sjöberg HE, Arver S & Bucht E. (1980) High concentration of immunoreactive calcitonin of prostatic origin in human semen. *Acta Physiol Scand* 110, 101–102.

* cited by examiner

Primary Examiner—Christopher R. Tate
Assistant Examiner—Roy Teller
(74) Attorney, Agent, or Firm—Joseph T. Leone, Esq.; DeWitt Ross & Stevens S.C.

(57) ABSTRACT

The hormone calcitonin promotes fertilizing ability in mammalian sperm and is useful for treatment of conditions of low fertility in humans and animals. Human, porcine or salmon calcitonin may be formulated in a pharmaceutical composition comprising a pharmaceutically acceptable carrier for topical application, e.g. as a cream or jelly containing up to 100 ng/ml or more of salmon calcitonin or up to 2 μg/ml or more of human calcitonin. Calcitonin may also be administered parenterally, orally, or nasally. For improving in vitro fertilization or artificial insemination methods calcitonin is added to sperm prior to use e.g. salmon calcitonin present at a concentration of from 5 to 50 ng/ml or human calcitonin at a concentration of from 20 to 200 ng/ml in the sperm preparation. Calcitonin levels in seminal plasma can also be used to diagnose infertility.

7 Claims, 3 Drawing Sheets

MODULATION OF SPERM FUNCTION

This invention relates to the treatment of mammalian sperm to modulate sperm function.

Although morphologically complete and capable of vigorous motility when they leave the male reproductive tract, mammalian sperm are not immediately able to fertilize oocytes. The acquisition of the capacity to fertilize an oocyte is termed capacitation. Once capacitated, sperm can undergo the acrosome reaction, a prerequisite for penetration of the zona pellucida and fusion with the oocyte plasma membrane; however sperm that have undergone a spontaneous acrosome reaction are non-fertilizing. A defect in these mechanisms results in a condition of infertility. At present there is no real treatment for this problem. The present invention is based on the discovery that the hormone calcitonin acts upon mammalian sperm to stimulate fertility.

Throughout the following description reference is made to various publications in the literature; a full reference list of these is given at the end of this specification.

Calcitonin is a 32-amino acid hypocalcemic hormone whose chief function is the regulation of $Ca^{2+}$ fluxes and metabolism. There are three main phylogenetic classes of calcitonin, teleost/avian, artiodactyl and rat/human (Pozvek et al, 1997.). Teleost/avian calcitonin is the most potent, with salmon calcitonin being widely used to treat human metabolic bone disorders. The term 'calcitonin' as used herein refers to calcitonin of any species including calcitonin of salmon, eel, chicken, porcine, bovine, rat and human origin, as well as precursors and derivatives which have similar activities in vivo and in vitro. Synthetic equivalents may also be used.

In the early 1980s several studies reported the presence of high concentrations of calcitonin in human seminal plasma. These findings prompted a number of preliminary studies addressing the possibility that calcitonin might have an effect on sperm, and one study reported that some concentrations of salmon calcitonin, but not human calcitonin, had a negative effect on human sperm motility. Since 1990 there has been no further published information on this subject.

Using a robust and well-characterized mouse in vitro capacitation system, we have determined that calcitonin elicits biologically important responses in mammalian sperm. For comparison, fertilization promoting peptide (FPP), which has been shown to stimulate capacitation and fertilizing ability in uncapacitated mouse sperm and then to inhibit spontaneous acrosome loss in capacitated cells, was used as a positive control. Cells incubated for a short time with/without calcitonin were assessed for changes in the chlortetracycline (CTC) fluorescence patterns that are known to reflect changes in sperm function. Because salmon calcitonin is considerably more bioactive than human calcitonin, we have used both forms but at different concentrations. Salmon calcitonin at 5 ng/ml and human calcitonin at 200 ng/ml and 20 ng/ml significantly stimulated capacitation, as did FPP, the positive control: there were more capacitated, acrosome-intact (B pattern) cells and correspondingly fewer uncapacitated, acrosome-intact (F pattern) cells. This change in distribution between the uncapacitated (non-fertilizing) and the capacitated (potentially fertilizing) cells in calcitonin-treated suspensions has also been shown to correlate with a significant stimulation of fertilizing ability. In addition the effects of salmon calcitonin on capacitated mouse sperm were evaluated, again using FPP as a positive control. Results indicated that salmon calcitonin, like FPP, significantly inhibited spontaneous acrosome loss, and that this response was abolished by the inclusion of pertussis toxin; the latter result indicates the possible involvement of G proteins. Taken together, these responses in mouse sperm indicate that calcitonin both stimulates the acquisition of fertilizing ability and then holds the sperm in a potentially fertilizing state.

The earlier study mentioned above reported that salmon, but not human, calcitonin when used at higher concentrations inhibited human sperm motility (Gnessi et al, 1984), but no such effect was seen on mouse sperm. In our hands, treated samples showed more vigorous sperm motility than untreated controls, consistent with the changes in CTC patterns observed. Our results provide convincing evidence that calcitonin elicits significant responses in mammalian sperm, indicative of its potential as an endogenous stimulator/regulator of sperm fertilizing ability in vivo. This finding provides a new therapeutic strategy for treating human male subfertility. It also has applications for improving the success of artificial insemination in agriculturally-important animal species.

DEMONSTRATION OF STIMULATORY EFFECT

Sperm Suspension Preparation for Chlortetracycline Analysis

The contents of cauda epididymides (3–4 cauda per ml of medium) from mature TO male mice (Harlan Olac, Bicester, U.K.) were released into 2 ml modified Tyrode's medium (Fraser, 1993) in 30 mm sterile culture dishes and allowed to disperse for 5 min. For studies on uncapacitated sperm, suspensions were then filtered through short columns of Sephadex G-25 (medium grade; Pharmacia, Uppsala, Sweden) to remove non-motile cells. Filtered suspensions were aliquotted out to different treatment groups, treated with nothing (control), calcitonin or FPP (as a positive control) and then incubated for 40 min. Salmon calcitonin was used at a final concentration of 5 ng/ml, human calcitonin was used at 200 ng/ml and 20 ng/ml and FPP was used at 100 nM. These short-term incubations were carried out in 0.5 ml plastic microcentrifuge tubes at 37° C. in an atmosphere of 5% $CO_2$, 5% $O_2$, 90% $N_2$. After the time allowed for incubation, an aliquot of each treated suspension was analysed using CTC to determine whether any effects on capacitation and hence acquisition of fertilizing ability could be observed. Three replicate experiments using uncapacitated sperm were carried out using salmon calcitonin and the higher concentration of human calcitonin (n=3); for the lower concentration of the human hormone, n=2.

In all experiments, a drop of each suspension was examined briefly for subjective motility evaluation. None of the experimental treatments had a deleterious effect on motility; judged subjectively, they all promoted more vigorous motility than that observed in untreated control samples.

Chlortetracycline Fluorescence Analysis

Chlortetracycline (CTC) fluorescence analysis was carried out as described by Green et al. (1994). Assessments were made on an Olympus BX40 microscope equipped with phase contrast and BX-FLA epifluorescence optics using the wide blue-violet excitation cube (U-MWBV). The excitation beam passed through a 400–440 nm band pass filter and CTC fluorescence was observed through a DM 455 dichroic mirror. In each sample, at least 100 sperm were classified as expressing one of three patterns: F, with fluorescence over the entire head, a pattern characteristic of uncapacitated (non-fertilizing), acrosome-intact sperm; B, with a fluorescence-free band in the postacrosomal region, a pattern characteristic of capacitated (potentially fertilizing), acrosome-intact sperm; AR, with dull or absent fluorescence over the whole head, a pattern characteristic of acrosome-reacted (non-fertilizing) sperm.

Sperm Preparation for in vitro Fertilization

The contents of the cauda epididymides from 2 mature TO male mice were released into 2 ml modified Tyrode's medium in 30 mm sterile culture dishes and allowed to disperse for 5 min. Suspensions were then divided into 3 treatment groups, each in a 30 mm sterile dishes, and treated with nothing (Control) or with calcitonin. As in the CTC experiments, salmon calcitonin was used at a final concentration of 5 ng/ml and human calcitonin at 200 ng/ml. Each suspension was overlaid with autoclaved liquid paraffin and incubated for 40 min at 37° C. in an atmosphere of 5% $O_2$, 5% $CO_2$, 90% $N_2$.

In vitro Fertilization Analysis

Mature female TO mice were induced to superovulate by intraperitoneal injections of 7.5 IU equine chorionic gonadotrophin and approximately 50 hr later with 5 IU human chorionic gonadotrophin (hCG). Approximately 15 hr post-hCG, oviducts were removed and cumulus masses containing the oocytes were released into medium covered with liquid paraffin. Preincubated sperm suspensions were diluted ~10 fold into medium of the same composition used for initial incubation (i.e., without or with calcitonin); 400 µl of diluted suspension were transferred to culture dishes, covered with liquid paraffin and oocytes were added. After 65 min coincubation, oocytes were transferred to small droplets of control medium and then at 75 min fixed with buffered formalin (4% formaldehyde in phosphate buffered saline).

Oocytes were stained with 0.75% aceto orcein, mounted and assessed (Fraser, 1993). They were considered to be fertilized if they had resumed the second meiotic division and contained a decondensing sperm head (n=4).

Results

The following results are described with reference to. FIGS. 1, 2, and 3 of the accompanying drawings.

Figure 1:
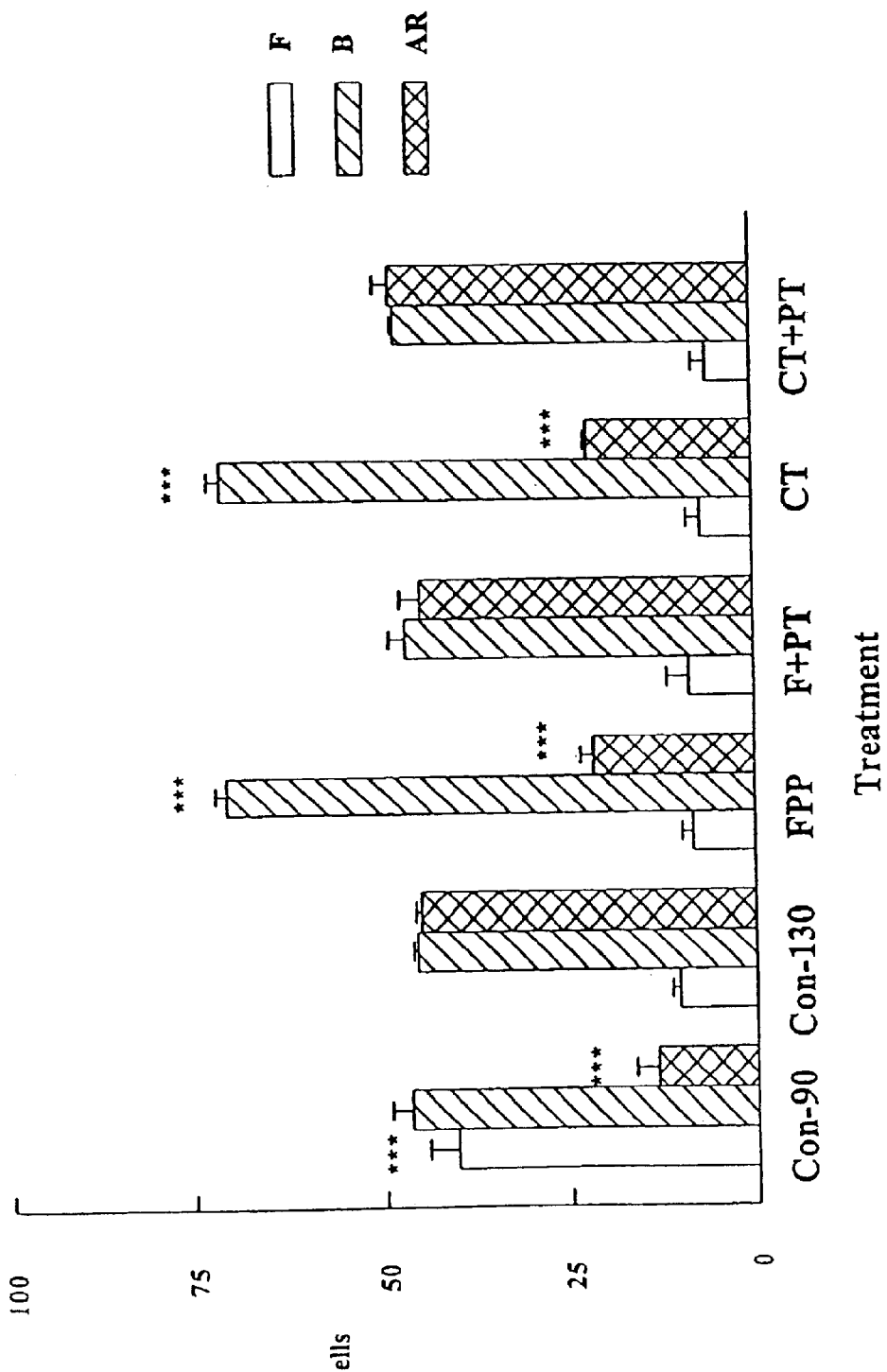
FIG. 1 shows that salmon and human calcitonin at 200 (Hi) and 20 (Lo) ng/ml significantly stimulate capacitation in uncapacitated mouse sperm.
Figure 2:
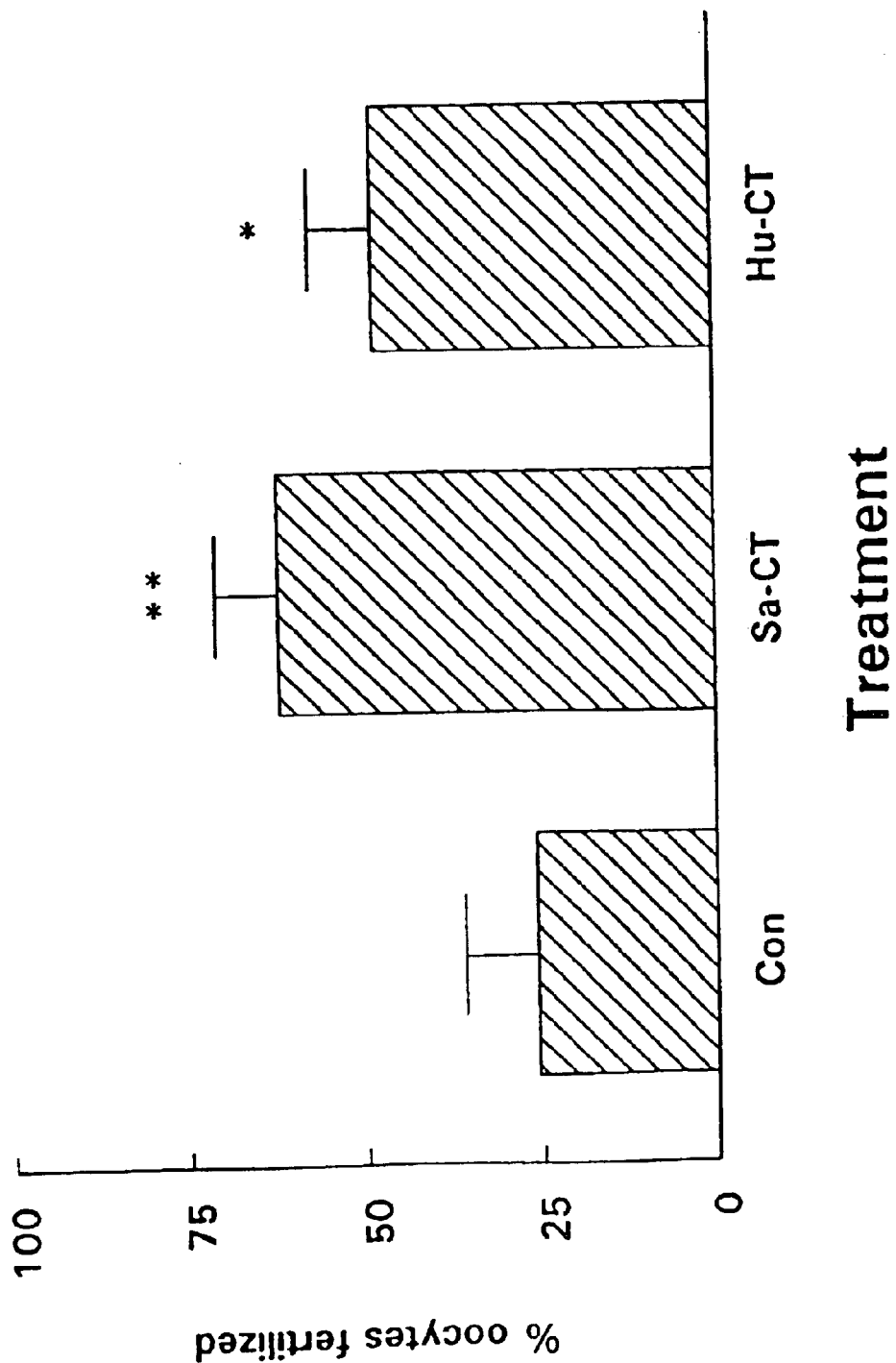
FIG. 2 shows that salmon calcitonin at 5 ng/ml and human calcitonin at 200 ng/ml significantly stimulate fertilizing ability of uncapacitated mouse sperm suspensions.

Uncapacitated epididymal mouse sperm treated with either salmon or human calcitonin capacitated at a significantly faster rate than sperm not treated with calcitonin (FIG. 1). This was evidenced by a significantly higher proportion (*$P<0.01$ for 5 ng/ml salmon CT, 200 ng/ml human CT and 100 nM FPP; $P<0.025$ for 20 ng/ml human CT) of B pattern cells (characteristic of capacitated, potentially fertilizing cells) and a corresponding significantly lower proportion of F pattern cells (characteristic of uncapacitated, non-fertilizing cells). It was also observed that calcitonin- and FPP-treated cells exhibited more active motility than untreated controls. The in vitro fertilization experiments demonstrated that significantly more fertilized oocytes were obtained with calcitonin-treated sperm (**$P<0.025$ for 5 ng/ml salmon CT and *$P<0.05$ for 200 ng/ml human CT) than with the untreated control sperm (see FIG. 2).

EFFECTS ON CAPACITATED SUSPENSIONS

Sperm suspensions were prepared as described earlier for CTC analysis and incubated for 90 min to allow capacitation. Suspensions were then filtered to remove non-motile cells and a sample was stained with CTC (Con-90). The remaining suspension was aliquotted out to different treatment groups and treated for 40 min with nothing (Con-130), 100 nM FPP (positive control), 100 nM FPP+100 ng/ml pertussis toxin (F+PT, negative control), 5 ng/ml salmon calcitonin (CT) and 5 ng/ml salmon calcitonin+100 ng/ml pertussis toxin (CT+PT); (n=3).

Figure 3:
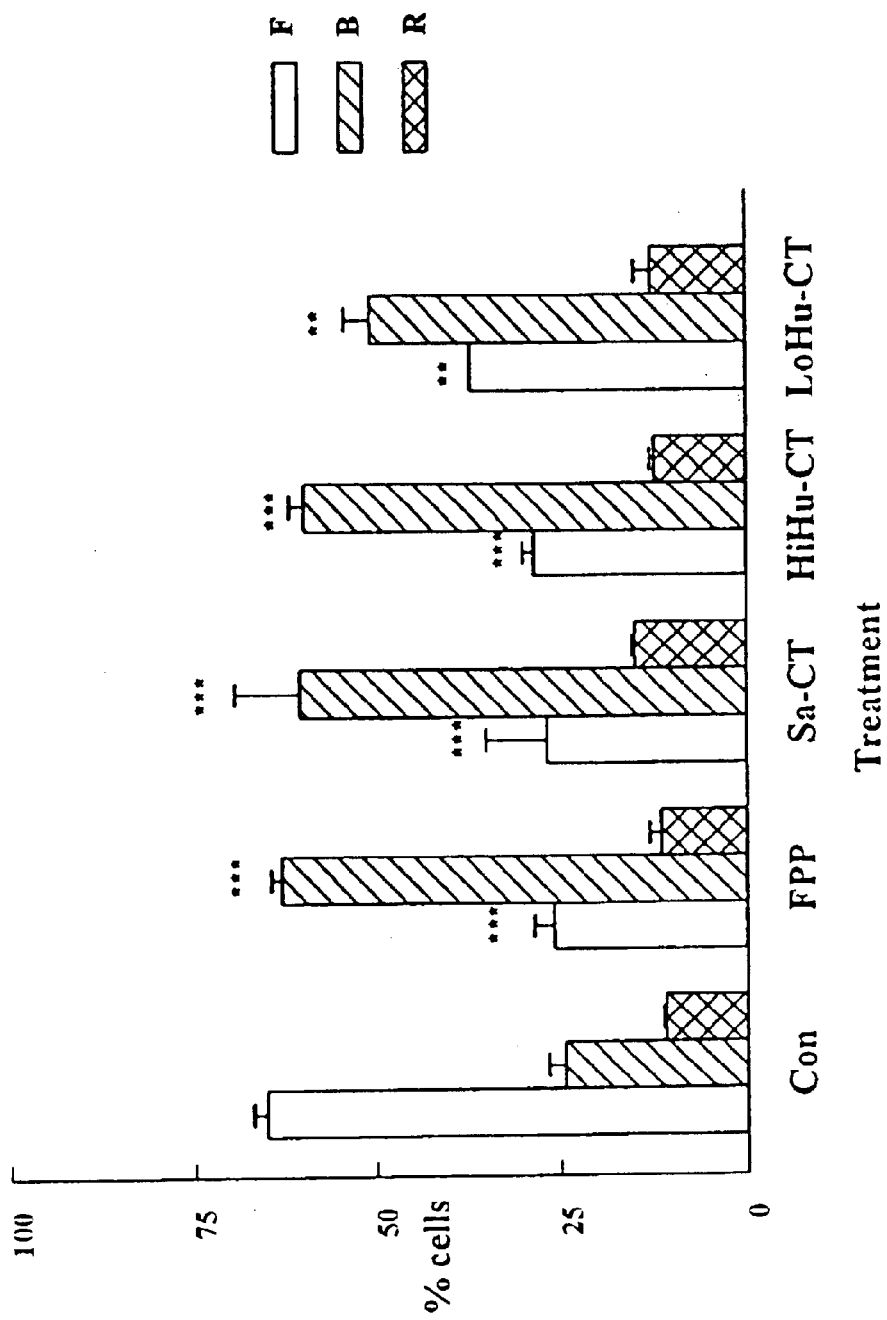
FIG. 3 shows that calcitonin and FPP inhibit spontaneous acrosome loss in capacitated mouse sperm and that this response is abolished by pertussis toxin.

Capacitated epididymal mouse sperm treated with both salmon calcitonin and FPP, the positive control, had a significantly lower incidence (***$P<0.01$) of spontaneously acrosome-reacted sperm than observed in the untreated control suspensions (FIG. 3). Furthermore, as with FPP, the inclusion of pertussis toxin at 100 ng/ml abolished the responses to salmon calcitonin, suggesting involvement of inhibitory G proteins in the response pathway. These results indicate that calcitonin first stimulates capacitation and the acquisition of fertilizing ability, then helps to maintain fertilizing potential by inhibiting spontaneous acrosome loss. Already acrosome-reacted sperm are unable to fertilize if they should come into contact with unfertilized oocytes.

CLINICAL APPLICATIONS

For the clinical applications of the present invention the amounts of calcitonin applied to sperm for effective improvement in fertilizing ability will depend on the extent to which any particular sperm is deficient in this respect; this can be readily determined by experiment using the correlative indicators mentioned above e.g CTC analysis. Some general guidance for particular applications are given below.

Diagnostic

Measurement of the calcitonin levels in seminal plasma may be used as a diagnostic procedure to identify men whose sperm require higher concentrations of calcitonin.

To quantitate calcitonin levels in seminal plasma, radioimmunoassays (RIA) employing commercially available anti-human calcitonin antibodies (Peninsula, Belmont Calif.) and iodinated human calcitonin are recommended. Human seminal plasma is obtained by centrifuging semen to remove sperm, lyophilised and reconstituted with RIA buffer (Hilton et al. 1998). Varying amounts of reconstituted seminal plasma and anti-human calcitonin antibodies are incubated at 4° C. for 16 hours. $^{125}$I-labelled calcitonin is then added and incubated overnight at 4° C. Simultaneously, a standard curve employing $^{125}$I-labelled calcitonin and 10–100,000 pg of human calcitonin is generated as described above. After separation of bound ligand from free as described by Hilton et al (1998), radioactivity from calcitonin/antibody complexes is measured on a gamma counter. Comparing counts from assays containing varying amounts of seminal plasma with values obtained from RIAs containing known amounts of calcitonin (standard curve) allows accurate determination of calcitonin concentration in seminal plasma.

An alternative, non-radioactive, method for quantitating calcitonin in seminal plasma is to use an enzyme-linked immunosorbent assay (ELISA). Seminal plasma should be prepared as described above, diluted, added to 96-well ELISA microtiter plates and incubated at 4° C. overnight. Residual fluid is removed, the plates are washed with phosphate-buffered saline and anti-calcitonin antibody is added. After incubation for 1–4 h at room temperature, the plates are washed and a secondary peroxidase-conjugated antibody is added; after incubation for 1–4 h at room temperature, the plates are again washed and peroxidase substrate is added. During a 30 min incubation, an orange-yellow colour will develop in the wells where peroxidase activity is present; the amount of coloured product is determined by reading plates in a microtiter plate reader. At the same time seminal plasma is being evaluated, a standard curve is generated by adding solutions containing 10–100,000 pg of calcitonin to the wells of a microtiter plate and treating as described above. The values obtained with the standard curve can be used to estimate the concentration of calcitonin in a fixed volume of seminal plasma.

The normal concentration of calcitonin in human seminal plasma is approximately 2 ng/ml (Sjöberg et al, 1980). If the concentration of calcitonin is found to be less than 1 ng/ml, then we recommend using exogenous calcitonin therapeutically in one of the ways described below.

Therapeutic

Fertilization promoting peptide (FPP), initially shown to stimulate mouse sperm fertilizing ability, has also been shown to stimulate human sperm fertilizing ability (Green et al., 1996). Therefore the fact that calcitonin, like FPP, significantly stimulates mouse sperm fertilizing ability strongly suggests that a similar effect occurs with human sperm. Consequently we propose the use of calcitonin both in vitro and in vivo.

Uses in vitro in Infertility Clinics

Procedures used in infertility clinics to prepare human sperm samples for either in vitro fertilization or intrauterine insemination involve washing the sperm free of seminal plasma and hence of calcitonin. Calcitonin can be added to these prepared sperm samples prior to their use. Motile sperm should be selected by layering unwashed semen on top of discontinuous gradients of a dense material such as PureSperm prepared in a suitable culture medium such as Earle's medium (e.g., 95, 70 and 50% PureSperm in Earle's), centrifuging for 5 min at 600 g and resuspending the pelleted cells to a concentration of $5\times10^6$ sperm/ml in fresh medium containing calcitonin. In our experiments using mouse sperm we have found that both salmon and human calcitonin work equally well, but the former is more potent and is used to treat humans with osteoporosis (see Pozvek et al., 1997). We recommend using salmon calcitonin at 5–50 ng/ml or human calcitonin at 20–200 ng/ml (final concentration in sperm preparations). Incubate sperm suspensions in the presence of calcitonin for 1–2 h at 37° C. in an atmosphere of 5% $CO_2$, then mix with oocytes if doing in vitro fertilization or inseminate into the uterine cavity for intrauterine insemination.

Uses in vivo

In order to increase the concentration of calcitonin available to sperm at the time they enter the female reproductive tract, one can use creams, jellies or pessaries containing calcitonin. To ensure that there is sufficient calcitonin to interact with ejaculated sperm which are released in seminal plasma, the concentration of calcitonin is preferably higher than that used for addition to prepared sperm in vitro. We recommend using preparations containing 5–100 ng/ml or more of salmon calcitonin or 1–2 μg/ml or more of human calcitonin.

An alternative approach is to administer exogenous calcitonin to men in order to raise their seminal plasma calcitonin levels. Calcitonin therapy for treatment of bone metabolism disorders is administered either by injection or intranasal spray. To increase seminal plasma calcitonin levels, we recommend daily subcutaneous injections of 250–500 IU salmon calcitonin or daily sniffing of 200–600 IU salmon calcitonin.

AGRICULTURAL APPLICATIONS

The present invention is applicable also to stimulating fertilizing ability of sperm in domestic animals. In many agriculturally important species (e.g., cattle, pigs, sheep) artificial insemination using either fresh or frozen/thawed semen samples is used to establish pregnancies. This is particularly important in controlled breeding programmes where it is commercially advantageous for farmers to have specific genetically-determined traits introduced into their stock. Because calcitonin stimulates fertilizing ability in mouse sperm, a similar stimulatory effect on sperm from these various animals can be expected. This may result in improved pregnancy rates, especially when frozen/thawed semen are being used. Mammalian sperm are frequently damaged by freezing and thawing and this results in lower fertility. By improving the performance of the viable sperm, calcitonin added to the sperm preparation used for insemination may promote a higher pregnancy rate per estrus cycle, reducing the number of cycles required to ensure conception and hence reducing the overall cost of artificial insemination. At the same time, semen from animals with highly desirable traits could be used to inseminate more females because fewer cycles would be needed to ensure conception in any one female. We recommend the addition of salmon calcitonin (final concentration of 50–200 ng/ml or more) or porcine calcitonin (final concentration of 200–500 ng/ml or more) to semen samples prior to insemination.

REFERENCES

Fraser L R. (1993) In vitro capacitation and fertilization. Methods Enzymol 225, 239–253.

Gnessi L, Silvestroni L, Baffri A, Moretti C, Panerai A E, Bonifacio V & Fraioli F. (1984) Salmon calcitonin inhibits human sperm motility in vitro. Biochem Biophys Res Commun 125, 199–204.

Green C M, Cockle S M, Watson P F & Fraser L R. (1994) Stimulating effect of pyroglutamylglutamylprolineamide, a prostatic, TRH-related tripeptide, on mouse sperm capacitation and fertilizing ability in vitro. Mol Reprod Dev 38, 215–221.

Green C M, Cockle S M, Watson P F & Fraser L R. (1996) Fertilization promoting peptide, a tripeptide similar to thyrotrophin-releasing hormone, stimulates the capacitation and fertilizing ability of human sperm in vitro. Human Reprod 11, 830–836.

Hilton J M, Mitchelhill K, Pozvek G, Dowton M, Quiza M, Sexton P. (1998) Purification of calcitonin-like peptides from rat brain and pituitary. Endocrinology 139, 982–992.

Pozvek G, Hilton J M, Quiza M, Houssami S & Sexton P M. (1997) Structure/function relationships of calcitonin analogues as agonists, antagonists, or inverse agonists in a constitutively activated receptor cell system. Mol Pharmacol 51, 658–665.

Sjöberg H E, Arver S & Bucht E. (1980) High concentration of immunoreactive calcitonin of prostatic origin in human semen. Acta Physiol Scand 110, 101–102.

What is claimed is:

1. A method of promoting fertilizing ability in mammalian sperm, the method comprising: contacting the sperm with a fertility-promoting amount of calcitonin.

2. A method of promoting fertilizing ability in mammalian sperm, the method comprising: contacting the sperm with a fertility-promoting amount of calcitonin selected from the group consisting of human, porcine, and salmon calcitonin.

3. A method for stimulating the capacitation of mammalian sperm and for holding the sperm in a potentially fertilizing state without spontaneous acrosome loss, the method comprising contacting the sperm with a capacitation-stimulating and acrosoine-loss-inhibiting amount of calcitonin.

4. A method of promoting male fertility of comprising applying calcitonin to sperm in an amount effective to stimulate capacitation of the sperm and to maintain the sperm in a potentially fertilizing state without premature acrosome loss.

5. A method of improving in vitro fertilization or artificial insemination which comprises adding calcitonin to sperm prior to use.

6. The method according to claim 5, in which salmon calcitonin is added at a concentration of from 5 to 50 ng/ml in a sperm preparation.

7. The method according to claim 5, in which human calcitonin is used added at a concentration of from 20 to 200 ng/ml in the a sperm preparation.

* * * * *